United States Patent [19]
Edwards et al.

[11] Patent Number: 6,139,707
[45] Date of Patent: Oct. 31, 2000

[54] PH ELECTRODE ARRANGEMENT

[75] Inventors: Stephen J. Edwards; Stephanie J. McIntyre, both of Pinner, United Kingdom

[73] Assignee: Eastman Kodak Company, Rochester, N.Y.

[21] Appl. No.: 09/181,101

[22] Filed: Oct. 28, 1998

[30] Foreign Application Priority Data

Feb. 4, 1998 [GB] United Kingdom .................. 9802288

[51] Int. Cl.⁷ .................................................. G01N 27/36
[52] U.S. Cl. .......................... 204/420; 204/433; 204/435; 205/787.5
[58] Field of Search ................................. 204/435, 420, 204/419, 433; 205/787.5

[56] References Cited

U.S. PATENT DOCUMENTS

| | | | |
|---|---|---|---|
| 3,111,478 | 11/1963 | Watanabe | 204/435 |
| 3,354,069 | 11/1967 | Jerrold-Jones et al. | 204/435 |
| 3,859,191 | 1/1975 | Frant et al. | 204/419 |
| 4,495,050 | 1/1985 | Ross, Jr. | 204/408 |

OTHER PUBLICATIONS

Dunt, *Ion–Selective Electrodes*, NBS Special Pub. 314, Nov. 1969, pp. 177–180.

Ives, et al, *Reference Electrodes*, 1961, pp. 179, 381–383.

*Primary Examiner*—T. Tung
*Attorney, Agent, or Firm*—Mark G. Bocchetti; Arthur H. Rosenstein

[57] ABSTRACT

A pH electrode arrangement comprises an inner wire electrode of silver sulfide, and a fill solution comprising a solution of sodium thiosulphate, a buffer, and an antioxidant. The arrangement has a fast response to a change in temperature, a half cell near ±500 mV, and an isopotential point near 7 pH.

4 Claims, 2 Drawing Sheets

PH ELECTRODE ARRANGEMENT

FIELD OF THE INVENTION

This invention relates to a pH electrode arrangement.

BACKGROUND OF THE INVENTION

Conventional pH electrodes usually contain a solution of potassium chloride and a pH buffer, to maintain the pH value, in a glass sheath. This fill solution, together with the pH sensing glass membrane formed in the sheath, defines the potential that is measured to determine the pH of the sample solution in which the electrode is immersed. The potential produced is the sum of the potential developed across the glass membrane and the potential of the internal reference electrode, usually a coated silver wire. The membrane potential is given by:

$$\text{glass membrane potential} = (pH_{inner} - pH_{outer})\frac{RT}{nF}$$

where $pH_{inner}$ and $pH_{outer}$ are the pH values of the solutions inside and outside the membrane respectively, R is the Universal Gas Constant, T is the temperature of the electrode system in °K, n is the charge on the ion, i.e. the number of electrons transferred in the reaction, and F is the Faraday Constant; and the reference electrode potential is given by:

$$Ag \text{ wire potential} = Ag \text{ standard potential} - \frac{RT}{nF}\log_n(\text{activity } Ag \text{ ion})$$

In most conventional electrode systems, the fill solution has an excess of chloride ions, and the silver ions present are derived from solid silver chloride that is attached to the electrode and/or is in solution. Thus, the activity of the silver is in equilibrium with the chloride activity via the solubility constant of silver chloride.

PROBLEM TO BE SOLVED BY THE INVENTION

At a fixed temperature and in constant pH, the membrane and reference electrode potentials settle quickly and remain substantially constant. If the pH of the solution is changed, the membrane potential changes rapidly. However, if the temperature changes, the activity of the silver ions in the fill solution changes with the change in solubility of the silver chloride. If the temperature increases, a steady temperature is not reached until the silver chloride has dissolved to the level defined by the solubility constant. This process can take many seconds, during which the potential lags behind the true, i.e. steady-state, potential. On the other hand, if the temperature decreases, silver chloride must precipitate to maintain the solubility constant. This process is faster than the former process, but still introduces a detectable lag.

The so-called Ross electrode, which is commercially available from ORION, disclosed in DE-A-3146066, avoids this temperature problem by using a fill solution that is a mixture of iodine and iodide and a platinum wire electrode, yielding a redox potential. Although the redox potential is still temperature dependent, since there are no solids that need to be dissolved, the temperature response of the wire is sufficiently fast in practice. However, this fill solution has the disadvantage that in time and on exposure to light, the ratio of iodine to iodide changes and this leads to slow drift of the potential. This is overcome, in practice, by using an iodine/iodide reference potential as well as the iodine/iodide internal electrode, but it does add to the complexity of the system.

Other fill solutions using soluble silver salts are known, notably silver acetate. This requires the use of a silver wire electrode. The internal potential consequently generated, however, is so large, due to the silver ion activity, that when combined with the membrane potential, the final electrode half cell potential is around 500 mV. The potential at pH 7 for this type of electrode would be approximately 400 mV with respect to a silver/silver chloride electrode. However, the standard measurement system requires a zero potential at a pH value of 7 (neutral), and is used to give maximum gain for a given analogue-to-digital converter, i.e. ±500 mV or ±7 pH units. Thus, this type of electrode cannot be used with the standard measurement system.

It is one object of the present invention to provide a pH electrode arrangement that not only responds quickly to a change in temperature, but that also is suitable for use with standard measurement systems.

SUMMARY OF THE INVENTION

In accordance with one aspect of the present invention, there is provided a pH electrode arrangement comprising an inner electrode having an outer surface of silver sulfide, a glass membrane, and a fill solution comprising a soluble silver complex.

Preferably, the electrode comprises a wire coated with silver sulfide.

The silver of the electrode fill solution may be in the form of a silver complex. Preferably, the fill solution may comprise a solution of sodium thiosulphate and a buffer, and preferably also an antioxidant.

ADVANTAGEOUS EFFECT OF THE INVENTION

The electrode arrangement of the invention responds relatively quickly to a change in temperature, since there is no solid material that needs to be dissolved, and the half cell potential is approximately equal to the normal value of ±500 mV with the isopotential point approximately at 7 pH.

BRIEF DESCRIPTION OF THE DRAWINGS

A pH electrode arrangement, in accordance with the present invention, will now be described, by way of example, with reference to the accompanying drawings, in which.

DETAILED DESCRIPTION OF THE INVENTION

Figure 1:
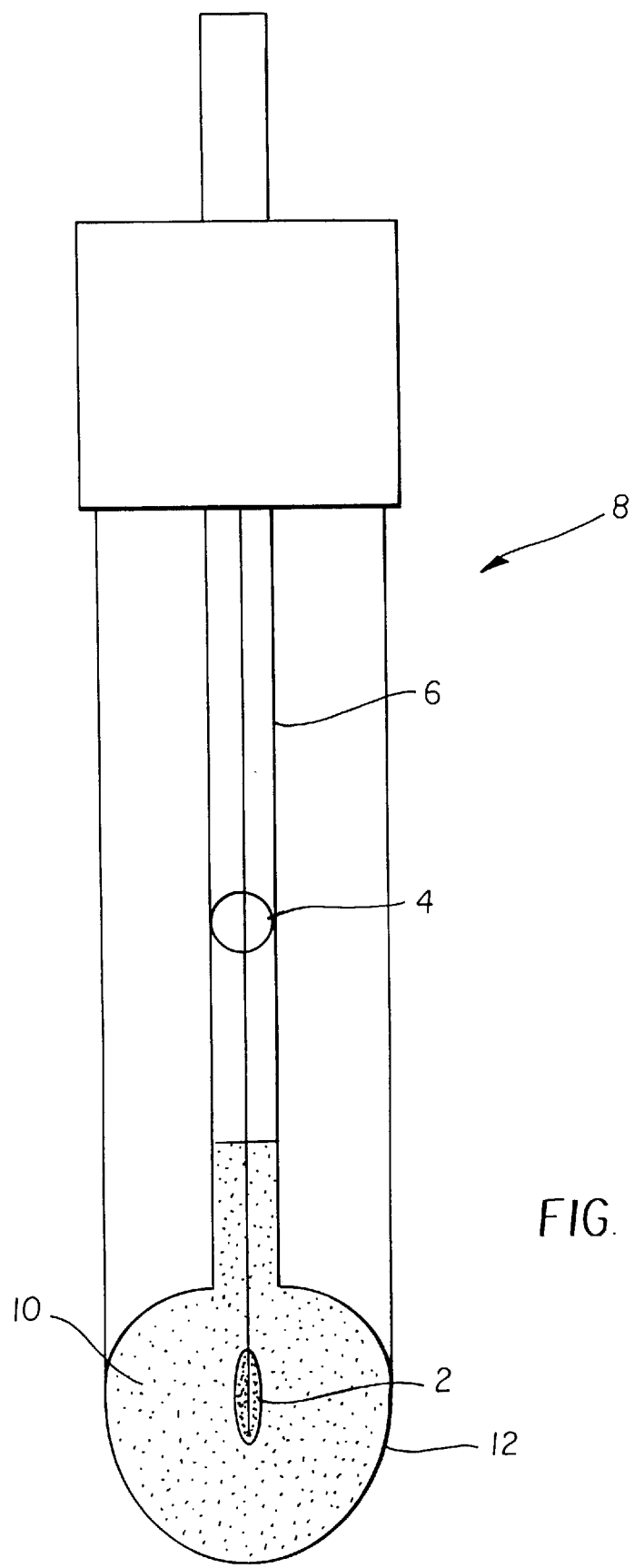
FIG. 1 shows the electrode arrangement.

Referring to FIG. 1, the electrode is formed with a silver wire 2 coated with silver sulfide sealed with a platinum seal 4 into a central stem 6 of the arrangement 8. The space around the electrode 2 is filled with a thiosulphate fill solution 10, and the extremity of the arrangement 8 is closed by a membrane glass 12.

By way of example, the arrangement 8 has a fill solution 10 containing 1.57 gm/l silver nitrate, 7 gm/l potassium bromide, 24.8 gm/l sodium thiosulphate, and 1.3 gm/l sodium sulfite adjusted to pH 7 with nitric acid. The arrangement may be used in conjunction with a commercial Ag/AgBr reference electrode to measure against. An isopotential point near 7 was achieved at approximately 120 mV.

Figure 2:
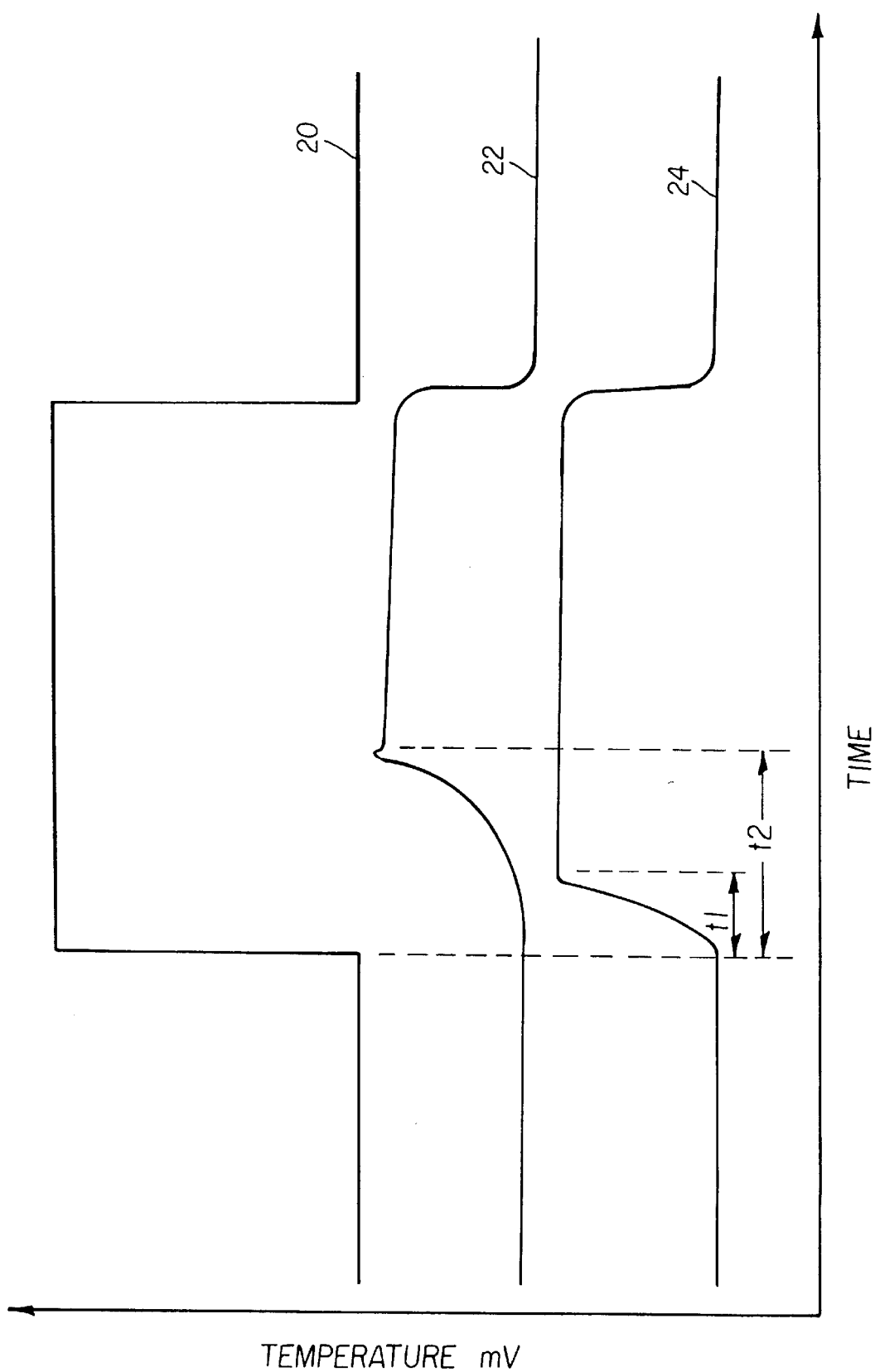
FIG. 2 is a series of graphs showing the temperature response of the electrode of FIG. 1 with respect to a conventional pH electrode arrangement.

FIG. 2 is a superpositioning on the same vertical axis, for convenience, of separated curves illustrating the comparative response of the electrode arrangement 8. The upper curve 20 shows an ambient temperature/time profile for a step increase from 40° C. to 70° C., followed by a period at constant 70° C., followed by a step decrease back to 40° C. The middle curve 22 shows the consequent voltage/time response of a conventional electrode, with a fill solution of 1 molar potassium chloride and phosphate 7 buffer. The lower curve 24 shows the corresponding response of the thiosulphate-filled pH electrode 8.

It is seen that the time delay t2 between the initial increase in temperature and the conventional electrode reaching its final potential, is significantly longer than the corresponding time delay t1 for the electrode 8, with a similar increase in output voltage of approximately 2 mV. As mentioned above, the time delay in response to a decrease in temperature is seen to be not significant. Thus, the electrode 8 will provide a more accurate indication of pH value under conditions of changing temperature.

What is claimed is:

1. A pH electrode arrangement comprising an inner electrode having an outer surface of silver sulfide, a glass membrane surrounding said inner electrode, and a fill solution comprising a soluble silver complex within said glass membrane.

2. A pH electrode arrangement according to claim 1, wherein the electrode comprises a wire coated with silver sulfide.

3. A pH electrode arrangement according to claim 1, wherein the fill solution comprises a solution of sodium thiosulphate and a buffer.

4. A pH electrode arrangement according to claim 1, wherein the fill solution comprises an antioxidant.

* * * * *